United States Patent [19]

Wilson et al.

[11] 4,312,815

[45] Jan. 26, 1982

[54] PREPARATION OF A ZINC CHELATE HAVING IMPROVED STABILITY

[75] Inventors: David A. Wilson, Richwood; Druce K. Crump, Lake Jackson; Freddie Griffin, Jr., Missouri City, all of Tex.

[73] Assignee: The Dow Chemical Company, Midland, Mich.

[21] Appl. No.: 136,008

[22] Filed: Mar. 31, 1980

[51] Int. Cl.$^3$ .............................................. C07F 3/06
[52] U.S. Cl. ............................. 260/429.9; 260/429 J
[58] Field of Search ........................... 260/429 J, 429.9

[56] References Cited

U.S. PATENT DOCUMENTS

| | | | |
|---|---|---|---|
| 2,624,760 | 1/1953 | Bersworth | 260/429 J |
| 2,943,100 | 6/1960 | Holstein | 260/429 J |
| 3,131,048 | 4/1964 | Balassa | 260/429 J X |
| 3,689,544 | 9/1972 | Scanlon et al. | 260/429 J X |
| 3,780,100 | 12/1973 | Scanlon et al. | 260/429 J X |
| 4,093,639 | 6/1978 | Habermeier et al. | 260/429 J X |

*Primary Examiner*—Helen M. S. Sneed
*Attorney, Agent, or Firm*—A. C. Ancona

[57] ABSTRACT

An improved process of preparing an aqueous solution of the zinc chelate of N-(2-hydroxyethyl) iminodiacetic acid wherein ammonia is added to the aqueous solution during its preparation to increase the solubility of zinc therein.

18 Claims, No Drawings

PREPARATION OF A ZINC CHELATE HAVING IMPROVED STABILITY

BACKGROUND OF THE INVENTION

It is well known that certain so-called trace elements, i.e., those which are required for plant growth, but in small amounts, can be added to the soil for utilization by plants. Some can also be added as a treatment to the leaves by spraying - indicated in the published literature as a "foliar spray". A good way to apply these trace elements is in the chelated form, e.g., a chelate of ethylenediaminetetraacetic acid (EDTA) or of N-(2-hydroxyethyl)iminodiacetic acid (HEIDA).

The zinc chelate of the latter chelating agent, while providing a good source of zinc, is limited in its applicability because of its low solubility in water. Trace metals are frequently applied as foliar sprays in water solution, but because of its low solubility it is not economical to apply Zn-HEIDA in this manner.

Zinc when applied as a foliar spray is used in its more soluble form as the chelate of EDTA, but the Zn-HEIDA is less costly to prepare and it would be beneficial if a way could be found to improve the solubility of its zinc chelate.

A method has now been found by which the water solubility of the zinc chelate of N-(2-hydroxyethyl)iminodiacetic acid is improved. The water solubility has been increased from about 0.5% Zn to more than 6% Zn by employing the method of the present invention for preparing the chelate. The improvement in the method comprises using ammonia, or ammonium hydroxide, in the preparation.

SUMMARY OF THE INVENTION

To prepare the zinc chelate having improved solubility ammonia (or $NH_4OH$) is added to an aqueous solution containing N-(2-hydroxyethyl)iminodiacetic acid or its disodium salt and a zinc compound. After solution is complete, the pH is adjusted to about 8 and the concentration of the solution is adjusted to contain about 5 wt. % zinc.

DETAILED DESCRIPTION OF THE INVENTION

In general the soluble zinc chelate of the present invention can be prepared by making an aqueous solution of (HEIDA-$Na_2$) the disodium salt of N-(2-hydroxyethyl)iminodiacetic acid, adding anhydrous ammonia, or ammonium hydroxide, adding a zinc compound, e.g., zinc chloride, and finally adjusting the pH to about 8 and the Zn concentration to about 5 wt. %. Such solutions have been kept at room temperature for a year and remained stable, i.e., no precipitate occurs.

Alternatively, the free acid (HEIDA) can be used to dissolve otherwise insoluble compounds of zinc, such as ZnO, Zn(OH)$_2$ and ZnCO$_3$, after which the solution is neutralized with ammonia.

Operable parameters of the preparation are a temperature of dissolution of about 20°-80° C. for a stirring time of about 15 minutes up to 5 hours.

One employs a ratio of chelant moiety to zinc of about one mole of chelant per mole of Zn and from 1.75 to 2.75 moles of ammonia per mole of zinc or mole of chelant. Less than 1.75 moles of the ammonia will cause precipitation while excess chelant will cause part of the chelate to be in the form of the 2:1 ratio of chelant:Zn, a much less soluble chelate, which will precipitate. Excess zinc leaves some of the zinc in unchelated form, which is also undesirable.

Temperatures lower than 20° C. are not beneficial while temperatures above 80° C. are unnecessary, too energy consuming, and cause the loss of ammonia from the solution.

The maximum amount of Zn-HEIDA chelate prepared according to the invention as in Example 1, in solution without a precipitate forming is one which is about 6% zinc, but, to err on the side of maintaining solubility of the chelate under various temperature conditions in storage and use, it is normally made available as a solution of chelate which contains about 5% zinc and the pH is adjusted to within a range of about 7.7 to 8.5.

We believe, although we do not wish to be limited by any theory that a single molecule of ammonia complexes with the zinc which in turn is coordinated by the chelating structure and that this is what solubilizes the Zn-HEIDA chelate. The structure may be represented as follows:

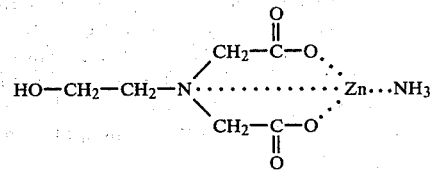

While a greater amount of ammonia is initially added in the preparation of the soluble chelate, only a single mole of ammonia is present per mole of zinc (or chelant) in the final product which has been neutralized to a pH of about 8.

The following comparative example shows the state of the art over which the present invention is an improvement.

COMPARATIVE EXAMPLE A

An aqueous solution (20.1 gms. of 27.5% active) of disodium-HEIDA (0.025 mole) was added to a reaction flask equipped with a stirrer, thermometer, and water cooled reflux condenser. An additional 302.4 gms. of distilled water was then added with stirring followed by 5.5 gms. of a 62.5% aqueous zinc chloride solution (0.025 mole). The zinc chelate precipitated from solution. It was determined that the solution contained less than 0.5 wt. % zinc. The pH was approximately 8.0.

The following example illustrates the process of the present invention in which the zinc chelate of HEIDA is made. Note that the solution of zinc chelate contains about 10 times the weight percent zinc as in comparative Example A.

EXAMPLE 1

An aqueous solution (160.7 gms. of 27.5% active) of disodium-HEIDA (0.20 mole) was added to a reaction flask equipped with a stirrer, thermometer, and water cooled reflux condenser. Ammonia (27.5 gms. of 29.7% solution - 0.48 mole) was added with stirring, followed by 40.4 gms. of a 67.6% zinc chloride solution (0.20 mole). The reaction mixture was stirred an additional hour, the pH adjusted with hydrochloric acid to about 8.1 and water added to a final zinc concentration of 5 wt. %. Solutions prepared in this manner have been stable for approximately one year.

The following comparative examples show the importance of having (1) sufficient ammonia present during the preparation of the zinc chelate solution, (B,C) and (2) insufficient Zn to form the desired chelate (D).

COMPARATIVE EXAMPLES B-D

B. Aqueous disodium-HEIDA (0.20 mole) was added to a reaction flask equipped with a stirrer, thermometer, and water-cooled reflux condenser. Aqueous zinc chloride (0.20 mole) was added as 40.4 g of 67.6% solution over a 5-minute period, followed immediately by the addition of aqueous ammonia (0.21 mole) to provide a pH 8.5. Water was added to provide a final zinc concentration of 5 wt. %. This solution began to develop a haze after 24 hours and became progressively more turbid with time.

C. Ammonia (0.50 mole) as a 29.7% $NH_3$ solution and 321.4 g. of a 27.5% aqueous disodium HEIDA solution (0.40) mole were added to a reaction flask equipped with a stirrer, thermometer and water-cooled reflux condenser. Aqueous zinc chloride, 80.8 g. of 67.6% solution (0.40 mole) was added and the reaction mixture was stirred for an additional hour. The pH was then adjusted to 8.1 with hydrochloric acid and water added to a final zinc concentration of 5 wt. %. Crystals began to form after standing for about five days. The infrared spectrum of these crystals was the same as the one obtained from the insoluble material formed in Comparative Example A.

D. Ammonia (0.48 mole) as a 29.7% solution and 176.8 g. as 27.5% aqueous disodium-HEIDA (0.22) mole were added to a reaction flask equipped with a stirrer, thermometer, and water-cooled reflux condenser. Aqueous zinc chloride, 40.4 g. as a 67.6% solution, (0.20 mole) was added and the reaction mixture stirred for an additional hour. The pH was adjusted to 8.2 with hydrochloric acid and water added to a final zinc concentration of 5 wt. %. This solution represents a 10 mole percent excess chelant based on a one to one molar zinc chelate solution. Crystals began to form in approximately three weeks. Infrared and elemental analysis of the crystals show the product to have a chelant to zinc mole ratio of 2/1.

Another way of preparing the zinc chelate of the present invention, starting with the HEIDA acid in place of its disodium salt, is shown in Example 2, below:

EXAMPLE 2

A salt-free zinc chelate solution was prepared from HEIDA (free acid), ZnO, and ammonia. Hydroxyethyliminodiacetic acid (35.4 g, 0.20 mole) and 150 gms. of distilled water were added to a round bottom reaction flask equipped with a stirrer, thermometer, water cooled reflux condenser, pH probe, and heating mantle. Some aqueous ammonia (28% $NH_3$) is added with stirring to provide a pH of approximately 3.5 followed by the addition of 0.20 mole of ZnO. The reaction mixture is heated to 60° C. and stirred for one hour and then additional ammonia solution is added to bring the total amount used to 0.48 moles $NH_3$. The reaction product is stirred for two more hours and then cooled. Excess ammonia may be removed if desired.

Either anhydrous ammonia or concentrated ammonium hydroxide (~28% $NH_3$) can be employed in the process of this invention. The zinc may be added as a salt or as an aqueous solution thereof. Thus, for example, solutions of $ZnCl_2$, $ZnSO_4$, $Zn(C_2H_3O_2)_2$ and $Zn(NO_3)_2$ may be used as in Example 1, while $Zn(OH)_2$, ZnO and $ZnCO_3$ may be employed as in the procedure of Example 2. The above salts are illustrative, not exhaustive of those useful in the process of the invention.

The HEIDA may be employed as the free acid as in Example 2 or as an alkali metal salt as in Example 1. For the neutralization step, other acids such as $H_2SO_4$, $HNO_3$ and acetic acid may be used. Alternatively the excess ammonia may be stripped from the solution by heat and or vacuum.

To show the stability of the zinc chelate prepared according to the invention as in Example 1, solutions containing various concentrations of zinc were made. The pH of the final solutions prior to storage or use was adjusted to about 8.1 or 8.2. These were observed periodically over a period of one year. Results are shown in Table I.

TABLE I

| Zn-HEIDA Solution (% Zn) | Time After which Crystals Present | Appearance After 1 Year |
|---|---|---|
| 5.0 | — | Clear |
| 5.5 | — | " |
| 6.0 | — | " |
| 6.25 | — | " |
| 6.5 | 7 days | Crystals pptd. |
| 7.0 | 3 days | " |
| 7.5 | 2 days | " |
| 8.0 | 1 day | " |

The effect of ammonia concentration during the preparation on the final Zn-HEIDA solution is shown in Table II.

TABLE II

| Moles HEIDA per Atom Zn | Moles $NH_3$/HEIDA | Appearance after 6 Mo. at 22° C. |
|---|---|---|
| 0.98 | 1.5 | small amount of crystals |
| " | 1.75 | slightly hazy |
| " | 2.0 | slightly hazy |
| " | 2.2 | clear solution |
| " | 2.4 | clear solution |
| 1.0 | 1.25 | many Crystals pptd. |
| " | 1.5 | small amount of crystals |
| " | 1.75 | slightly hazy |
| " | 2.0 | slightly hazy |
| " | 2.2 | clear solution |
| " | 2.4 | clear Solution |
| 1.02 | 1.5 | small amount of crystals |
| " | 1.75 | slightly hazy |
| " | 2.0 | clear solution |
| " | 2.2 | clear solution |
| " | 2.4 | clear solution |
| 1.10 | 2.2 | crystals present* |

*Comparative Example D.

The freeze-thaw stability of this product is very good. Samples were frozen at −30° C. and then one sample was thawed each week over a 6-week period. The thawing time (~1 hour) remained essentially constant regardless of the length of time the material remained frozen.

In light of the data in Tables I and II it is apparent that the best solution for storage and/or use contains 5.0 to 6.25 weight percent zinc, and sufficient ammonia to provide an initial mole ratio of $NH_3$/HEIDA of 1.75 to 2.75. The final product should have a pH of from about 7.7 to 8.5.

We claim:

1. In the process of making the zinc chelate of N-(2-hydroxyethyl)iminodiacetic acid wherein the mole ratio of chelant/zinc is substantially 1 and wherein a zinc salt, oxide or hydroxide is added to an aqueous solution of said chelant, the improvement which comprises adding to said aqueous solution sufficient ammonia, or ammonium hydroxide, to provide from about 1.75 to about 2.75 moles of $NH_3$ per mole of said chelant.

2. The process of claim 1 wherein zinc and the N-(2-hydroxyethyl)iminodiacetic acid are present in the mole ratio of from about 0.98/1.0 to about 1.02/1.0, respectively.

3. The process of claim 1 wherein the final chelate solution is adjusted to a pH of within the range of 7.7 to 8.5.

4. The process of claim 3 wherein the pH is 7.9 to 8.2.

5. The process of claim 3 wherein the concentration of zinc in the solution is adjusted to about 5%.

6. An aqueous solution of zinc chelate containing about 5% zinc by weight which has been prepared by adding $NH_3$ to an aqueous solution containing a zinc salt, oxide or hydroxide and N-(2-hydroxyethyl)iminodiacetic acid.

7. The process of claim 1 wherein the chelant employed is a dialkali metal salt of N-(2-hydroxyethyl)iminodiacetic acid.

8. The process of claim 1 wherein the chelant is the free acid.

9. The process of claim 7 wherein the zinc salt is a water soluble zinc salt.

10. The process of claim 9 wherein the zinc salt is selected from $ZnCl_2$, $ZnSO_4$, $Zn(C_2H_3O_2)_2$ and $Zn(NO_3)_2$.

11. The process of claim 8 wherein the zinc salt, oxide or hydroxide is relatively water insoluble.

12. The process of claim 11 wherein the zinc salt, oxide or hydroxide is selected from $ZnO$, $Zn(OH)_2$ and $ZnCO_3$.

13. The process of claims 3 or 4 wherein the pH is adjusted by adding an acid to the chelate solution.

14. The process of claims 3 or 4 wherein the pH is adjusted by evaporating ammonia from the chelate solution.

15. The process of claim 7 wherein the order of addition of reactants is chelant, ammonia and zinc salt, oxide or hydroxide.

16. The process of claim 8 wherein the order of addition is chelant, zinc salt, oxide or hydroxide and ammonia.

17. A soluble zinc chelate of hydroxyethyliminodiacetic acid which contains ammonia.

18. The chelate of claim 17 wherein the molar ratio of chelant to zinc to ammonia is approximately 1:1:1.

* * * * *